(12) United States Patent
Latham

(10) Patent No.: US 7,785,359 B2
(45) Date of Patent: Aug. 31, 2010

(54) THERAPEUTIC COOLING DEVICES

(75) Inventor: Jeffrey Wade Latham, San Marcos, TX (US)

(73) Assignee: Traumatec, Inc., Houston, TX (US)

(*) Notice: Subject to any disclaimer, the term of this patent is extended or adjusted under 35 U.S.C. 154(b) by 0 days.

(21) Appl. No.: 10/080,351

(22) Filed: Feb. 21, 2002

(65) Prior Publication Data

US 2002/0103520 A1  Aug. 1, 2002

Related U.S. Application Data

(63) Continuation-in-part of application No. PCT/US00/29509, filed on Oct. 26, 2000, which is a continuation of application No. 09/215,988, filed on Dec. 18, 1998, now Pat. No. 6,183,501.

(51) Int. Cl.
*A61F 7/00* (2006.01)

(52) U.S. Cl. .................. 607/111; 607/109; 607/114

(58) Field of Classification Search ......... 607/104–112, 607/114; 602/2, 22, 74, 14, 21
See application file for complete search history.

(56) References Cited

U.S. PATENT DOCUMENTS

| | | | |
|---|---|---|---|
| 4,190,054 A | | 2/1980 | Brennan |
| 4,204,543 A | | 5/1980 | Henderson |
| 4,356,709 A | | 11/1982 | Alexander |
| 4,382,446 A | | 5/1983 | Truelock et al. |
| 4,538,597 A | | 9/1985 | Lerman |
| 4,552,149 A | | 11/1985 | Tatsuki |
| 4,552,964 A | | 11/1985 | Ramachandran |
| 4,576,169 A | | 3/1986 | Williams |
| 4,706,658 A | * | 11/1987 | Cronin .................. 602/13 |
| 4,732,144 A | | 3/1988 | Cunanan |
| 4,750,493 A | | 6/1988 | Brader |
| 4,805,619 A | | 2/1989 | Swearingen |
| 4,815,144 A | | 3/1989 | Martin |
| 4,886,063 A | * | 12/1989 | Crews ................... 607/112 |
| 5,053,003 A | * | 10/1991 | Dadson et al. ........... 604/28 |
| 5,054,475 A | | 10/1991 | Calabrese et al. |
| 5,129,391 A | * | 7/1992 | Brodsky et al. ......... 607/110 |
| 5,152,285 A | * | 10/1992 | Gnegy ................... 607/108 |
| 5,197,292 A | | 3/1993 | McPherson |
| 5,211,623 A | | 5/1993 | Sarkozi |
| 5,261,399 A | | 11/1993 | Klatz et al. ............. 607/104 |
| 5,267,945 A | * | 12/1993 | Doctor et al. ............ 602/14 |
| 5,295,949 A | * | 3/1994 | Hathaway ............... 602/18 |

(Continued)

OTHER PUBLICATIONS

The Multiple Sclerosis Association of America, "Multiple Sclerosis and Cooling," 2$^{nd}$ Ed., 2001, 12 pp.

(Continued)

*Primary Examiner*—Roy D Gibson
(74) *Attorney, Agent, or Firm*—Edwin S. Flores; Daniel J. Chalker; Chalker Flores, LLP

(57) ABSTRACT

A thermal regulatory system to reduce swelling caused by trauma to a variety of tissues and limbs is provided. One or more substantially flexible, at least partially thermally conductive housing containing optionally activatable thermal regulatory medium may be coupled with one or more applicator, such as a splint, that is adapted to apply the medium housing to the tissue. Methods of therapeutically regulating tissue temperature are also provided.

6 Claims, 15 Drawing Sheets

U.S. PATENT DOCUMENTS

| | | | |
|---|---|---|---|
| 5,327,585 A | | 7/1994 | Karlan |
| 5,412,624 A | * | 5/1995 | Yocom ........................ 368/156 |
| 5,415,624 A | * | 5/1995 | Williams ..................... 602/21 |
| 5,437,612 A | | 8/1995 | Moore et al. |
| 5,557,807 A | | 9/1996 | Hujar et al. |
| 5,769,806 A | * | 6/1998 | Radow ......................... 602/41 |
| 5,871,526 A | * | 2/1999 | Gibbs et al. ................. 607/104 |
| 5,897,581 A | | 4/1999 | Fronda et al. ............... 607/109 |
| 5,913,885 A | | 6/1999 | Klatz et al. ................. 607/104 |
| 5,957,964 A | | 9/1999 | Ceravolo ..................... 607/109 |
| 6,141,801 A | * | 11/2000 | Helenick ....................... 2/159 |
| 6,409,746 B1 | * | 6/2002 | Igaki et al. .................. 607/109 |
| 6,561,995 B1 | * | 5/2003 | Thibodo, Jr. ................. 602/22 |
| 6,602,213 B1 | * | 8/2003 | Figley ............................ 602/5 |
| 6,840,955 B2 | * | 1/2005 | Ein ............................. 607/108 |
| 2002/0103520 A1 | * | 8/2002 | Latham ....................... 607/108 |

OTHER PUBLICATIONS

Texan Corporation, Ad for "P.A.C. Tubing personal cooling system," Mar. 1999, 2 pp.

Ad for Microclimate Systems, "Body Temperature Management," 1990, 1 pp.

Dreyfuss I, "When heat's on, bike helmets are still cool, researcher says," The Associated Press, Aug. 7, 1997, 2 pp.

Baker DG, "Searching for Ways to Stay Cool with MS," Multiple Sclerosis Quarterly Report. 1999, 2 pp.

Baker, DG, "Cooling: A Simple Therpateutic Tool for Multiple Sclerosis," Multiple Sclerosis Quarterly Report, vol. 17, No. 4, Dec. 1998, 4 pp.

Shaughnessy L, "The Effects of Heat on MS," Center for Neurological Diseases/Rocky Mountain MS Center, 1999.

* cited by examiner

FIG. 5
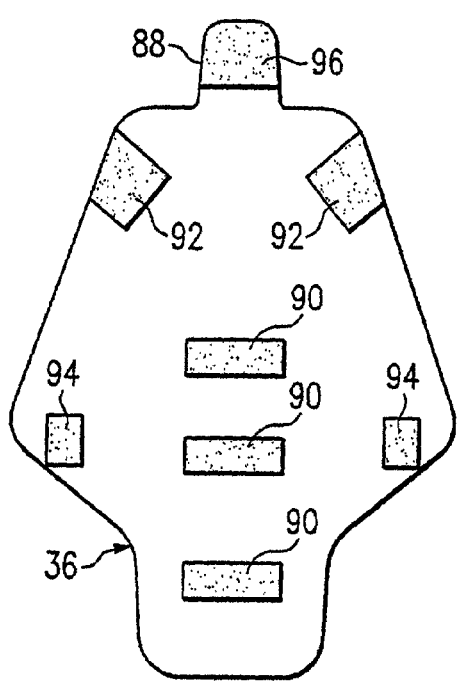
FIG. 5A
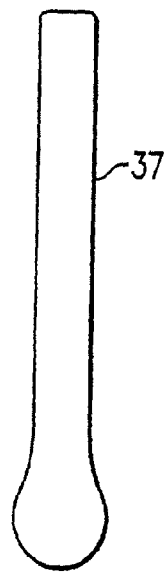
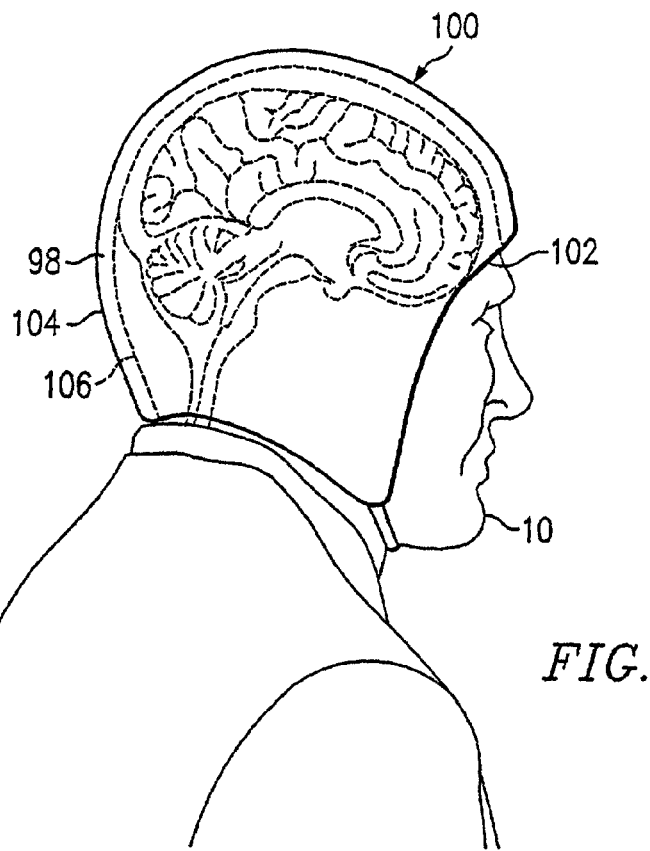
FIG. 6

THERAPEUTIC COOLING DEVICES

This application is a continuation-in-part of, and claims priority from, co-pending PCT patent application Ser. No.: PCT/US00/29509, filed Oct. 26, 2000, which is a continuation of U.S. patent application Ser. No. 09/215,988, filed Dec. 18, 1998, now issued as U.S. Pat. No. 6,183,501 B1.

TECHNICAL FIELD OF THE INVENTION

The present invention relates, in general, to the field of therapeutic cooling with substantially rigid devices, and more particularly, to devices for cooling various parts of the anatomy to reduce trauma, pain or blood flow to those areas.

BACKGROUND OF THE INVENTION

Without limiting the scope of the invention, its background is described in connection with brain and spinal cord treatment, as an example.

The brain and spinal cord form the central nervous system (CNS), the body's chief controlling and coordinating centers. The brain, which is housed in the skull, is the major organ of the body for control of all the body's voluntary and involuntary activities. The principal parts of the brain are the brain stem, the diencephalon, the cerebrum, and the cerebellum. Cranial bones and the cranial meninges protect the brain and cerebrospinal fluid serves as a shock absorber for the brain and circulates nutritive substances from the blood to the brain. A large round hole called the foramen magnum is located at the bottom of the skull. It is through the foramen magnum that the spinal cord passes down from the brain into the spine. The spine is a bony column which serves as a protective surrounding for the spinal cord.

When an area of the body collides with an external source in its surroundings, severe trauma and swelling of the tissue may occur in the injured area. To reduce swelling, treatment often consists of lowering the temperature of the injured area.

Lowering temperature is often achieved by applying a cold element or substance to the injured area. In some instances, the treatment has been as simple as applying ice to the location of the injury. More sophisticated methods have included applying cold packs to the injury. Heretofore, in this field, cold therapy has generally been limited to the limbs of the body including the leg (particularly the knee), the arm, and the shoulder. Treatment of this type has generally been applied most consistently in situations involving athletic injuries. Cold therapy has also been used for aesthetic purposes such as applying cold packs to the face to reduce bags under the eyes and for purposes of reducing the pain of headaches. Therapy has generally required refrigeration of the packs.

When the brain or spinal cord is traumatized due to injury, the extent of the trauma to the brain or spinal cord is not always readily apparent. The collision of an individual's head with external surroundings causes the brain to collide with the individual's skull, which may produce swelling of the brain. Swelling can restrict the flow of fluids that normally circulate around the brain and, potentially, cause the fluids to accumulate and therefore compress the brain down into the floor of the skull and cervical bone of the spine. The collision of the individual's head or body with external surroundings may cause injury to the spinal cord and result in swelling. To reduce the effects of this secondary trauma, the present invention can be placed over the head, neck, and spinal regions to lower the temperature in those areas and help reduce swelling. The reduced swelling of the brain reduces the potential for more serious injury to the individual.

Therefore, there is a need for a device that may be easily transported and applied in emergency situations but may also be used in rehabilitative environments. Also, there is a need for a device that requires no special storage conditions such that implementation of such a device requires extensive redesign of, or requires, additional space for storage facilities. Furthermore, there is a need for a device that may be flexibly and easily adapted to an individual at the scene of an accident while not adding additional stress or pressure on the individual.

SUMMARY OF THE INVENTION

In one embodiment, the present invention provides a cooling system that includes a head device and a neck brace or one in the same. The head and neck splint of the present invention may be combined to facilitate both cooling and splinting with substantial rigid support in a unitary device. The head device has a top panel and a back panel; each panel capable of housing a cold element to facilitate cooling. The top panel may include one or more fastening devices to secure the head device to the head of the individual. The front panel may also include one or more orifices to facilitate access to the ears of the individual. The back panel of the head piece may include one or more fastening devices and a bottom appendage; the fastening device being positioned to come into contact with the one or more fastening devices located on the front panel for complete coverage of the head and over the carotid arteries. The back panel may be elongated by attaching a back panel strip that covers the back along the spinal cord for cooling.

The cooling system may also include a neck brace having front and back brace members and a chin support. The neck brace may further include one or more orifices that allow air to circulate to reduce heat buildup which may cause sweating and discomfort of the individual. The neck brace may also have a hole for, e.g., facilitating a tracheotomy to assist the individual in breathing, if necessary. The neck brace may also include a fastening device to secure the neck brace to the individual and to support the head device.

In another embodiment, the cooling system of the present invention may be a one-piece head device. The head device includes an opening for facial exposure and is capable of housing a cooling element. The head device further includes a flexible material.

A further embodiment provides a cooling system having a top panel with one or more cooperating fasteners and a right side and a left side corresponding to the right side and the left side, respectively, of the individual. A first elongate neck member extends from the right side and a second elongate neck member extends from the left side so the neck members are disposed substantially over the carotid arteries of the neck when worn by said individual. The system further provides activatable cooling medium housed in the top panel and the neck members so the cooling medium cools the head and cools blood flowing to the head from the carotid arteries of the neck upon activation of the cooling medium. The system may be adapted for use with recreational, sports or occupational head protection.

A still further embodiment provides a system for cooling blood flowing to the brain of an individual from the neck by means of a flexible neck member housing activatable cooling medium. The flexible neck member includes a body and first and second members extending laterally from the body. The first and second members further have cooperating perimeter contours. A spine support portion extends from the body between said first and second members. Fasteners are provided on the first and second members. The first and second members wrap around the neck of the individual so that the first and second members are fastenable together by the fasteners and so that the cooperating perimeter contours of the first and second members cooperate to form an orifice that allows access to the front of the neck of the individual. Activation of the coolant medium cools blood flowing to the brain from the neck.

In yet another embodiment, the cooling system of the present invention comprises a cooling device and a cooling element system. The cooling element system includes a connecting mechanism whereby the cooling element may enter the cooling device, a storage device for housing said cooling element, and a release system.

The present invention allows Emergency Medical Services (EMS) personnel to monitor bleeding of the individual, if any. The present invention also facilitates management of the airway by allowing for tracheotomy treatment. Because of the facial opening of the present invention, the eyes, nose and mouth of the individual may be monitored.

A form-to-fit compression cooling wrist splint is provided that simultaneously stabilizes the wrist and gently compresses swelling tissue. Coolant-filled panels or chemical cold packs that may be located on the interior or exterior of the splint enable cooling. Alternatively, a substantially rigid splint support may be incorporated on the exterior of a cooling panel or in the interior of the cooling panel. The splint immobilizes the joint while the cooling element reduces edema. The splint may be attached to or otherwise coupled with either a passive or an active cooling system.

An example of a passive cooling system is a coolant gel that may be stored in a refrigerator or freezer and which tolerates repeated cooling and warming. Another passive cooling system may be a contained chemical system in which mixing chemicals initiates an endothermic reaction. A passive cooling system may be adapted for single use, disposable packs or for multiple use regenerating packs. An active cooling system, for example, may include a circulating system of fluid, chemicals or cold air. While the present invention is described primarily in terms of cooling thermal regulation, it will be understood by those skilled in the art that the present invention may adapted to provide warmth with the selection of suitable passive or active thermal regulatory media and equipment.

Controls to regulate skin temperature and monitors to measure skin temperature may be included with the thermal regulatory splint embodiments of the present invention. Velcro, snaps, ties, zippers or other fasteners may be adapted to fasten the cooling splint to the wrist. The splint may be formed to fit many different sized wrists by manipulating deformable but substantially rigid support material of the splint. The cooling splint embodiment reduces swelling tissue such as occurs in carpel tunnel syndrome. The invention also contemplates a warming splint embodiment wherein coolant is replaced with a suitable heat transfer material.

A form-to-fit cooling compression splint for the knee or elbow is provided by the present invention. A deformable yet substantially rigid splint material stabilizes or immobilizes and gently compresses a swelling joint. To dissipate edema, cold panels or chemical cold packs may be fastened to the inside or outside of the splint with Velcro, snaps or other suitable fastener, or coolant packs may be inserted in pocket partitions of the splint system. Alternatively, the rigid splint material may be incorporated on the exterior to form at least a partial shell or in the interior of the cooling panels. In one embodiment, the splint may have passive cold chemical activation packs or refrigeration gel packs. In another embodiment, the cooling splint system may be fluidly connected to an active coolant circulating system by which cold fluid or cold air may be circulated by conduits through the cooling panels and back through a refrigerator housing to regenerate the coolant. To fit different sized knees or upper or lower legs, the splint may be fabricated of flexible or deformable, yet substantially rigid material. The device may be adapted to a smaller size for the elbow joint or lower extremity limbs such as the calf or shin.

A hand or finger splint embodiment may be worn like a glove or mitten by burn or trauma patients for controlling edema. Coolant may be supplied to the hand or finger splint embodiment as described herein for the other embodiments. Some injuries to the hand or finger may make it difficult to slide a glove or mitten over the hand. The glove, therefore, may be adapted to provide selectively fastenable and unfastenable portions so that the glove may be wrapped around an injured hand rather than slid over the hand. The glove may provide sufficient freedom of movement so that the hand may be opened and closed for physical rehabilitation exercises during cooling treatment.

A finger splint embodiment may be fitted over the finger in a manner similar to the toy called Chinese handcuffs or finger trap. The sleeve of the splint may be adapted to fit several fingers and may slide on to or wrap around each individual finger painlessly. As with the other embodiments described herein, the finger splint may be adapted for active or passive cooling. The hand or finger splint may be useful for treating jammed, sprained, fractured or swollen hand or fingers and may provide a substantially rigid structure for stiff splinting. The splint system may be adapted to provide warming heat to treat arthritic joints, poor circulation or certain disabilities arising from stroke.

The present invention also provides an ankle compression cooling splint embodiment. Panels housing coolant packs or coolant conduits may be configured in a figure "8" form to stabilize and cool the ankle. Additionally, rigid splint or brace structures attached to the exterior of the panels by Velcro, straps, laces, snaps or the like help immobilize the ankle. The splint may be cooled by passive gel, air, chemical or active circulation. Alternatively to the figure "8" form, the panel may be adapted to wrap around the ankle and equipped with a substantially rigid brace. Cooling may be provided by a tubular coolant panel that slides over or wraps around the ankle like a tube sock to provide cooling to the foot when worn inside a boot or shoe.

A cooling adaptable unitary piece cervical collar immobilizer with a substantially rigid support is another embodiment of the cooling system of the present invention. Any combination of splinting and cooling the neck and carotid arteries with separate cooling packs that are not attached to the rigid support are applicable in this embodiment. A substantially rigid support may be adapted with holes or pouches in the front, back and sides of the brace to allow access to the patient's neck for external cooling packs or medical monitoring. A substantially rigid structure may be located inside the cooling pack and be formable to snugly fit a patient's neck.

To stabilize the head, wedge-shaped coolant packs or cooling system may be provided with a backboard neck-cooling embodiment of the present invention so that the cooling wedges may be placed between the splint and the neck. The cooling system may be active or passive with cold gel, chemical, fluid or air. A self-contained cooling circulation system kit of the present invention may be installed in an ambulance on an interior side panel, for example, or an active cooling system of the invention may be connected to the air conditioning system of the ambulance. Additionally, the circulation system may be permanently mounted on or in a wall of a hospital such that active coolant may be plugged into the collar splint embodiment. The coolant may be air, water, gel, passive or active circulating fluid.

A wheel chair cooling or warming system embodiment includes a passive panel or active circulation cooling system fitted into a wheel chair seat cushion and/or back cushion. The thermal regulation system may be attached to the chair to maintain free and independent roaming mobility for the user. The thermal regulation system may provide intermittent circulation modalites with temperature and pressure controls, including, for example, a thermostat, to prevent pressure sores. The cushion embodiment may find utility not only for wheelchairs but also for thermal regulation in extreme environmental conditions including sports arena benches.

A Thoracic, Lumbar, Sacral Orthopedic (TLSO) splint cooling system of the present invention is provided that may include a cooling system for a splint to stabilize the upper torso. The TLSO embodiment may include a substantially rigid support and flexible cooling system panels attached to the inside of the rigid splint or brace. The TLSO embodiment may be used for physical rehabilitation purposes.

Micro-fiber cooling matrix fabric has hollow fibers filled with coolant. The hollow fibers are typically no larger in internal diameter than a pin whole. The fabric may be useful in situations that require temperature regulation in an unregulated environment. Typically, the fabric is durable and may be elastic or flexible yet remain dry for comfortable wear. When worn, body movement circulates cooling fluid stored inside the fabric fibers. The fabric fibers may be vinyl, plastic polyester or other synthetic fabric, for example. The coolant fabric may be woven in a blend with natural fibers to provide comfort. The coolant may comprise passive fluid coolant combined with air much like the radiator of a car. Ordinary fabrics, such as cotton, wool, silk, synthetics or blends, may be woven or sewn with the cooling fiber to add a designer look and quality. A garment of the cooling fabric may be useful for warm environments to cool an individual or it may be combined with splints and soft pads inside substantially rigid splints. The fabric may be used in clothing, undergarments, shoes, hats, caps or protective gear. The fabric may also be used in air conditioning systems in a vehicle, computer or home. Air blown across or through the matrix provides an environmental cooling system. The fabric may be utilized as a thermal filtration system to cool any type of fluid. Of course, the hollow-fiber fabric of the present invention may be adapted to provide warmth with the selection of suitable thermal regulatory medium and equipment.

A cooling adhesive bandage embodiment of the invention is provided for small cuts on the hand, finger or body. Similar to the common adhesive bandages, the present invention has the advantage of providing a small thin gel pack on the interior or exterior of the adhesive strip to cool a superficial wound and reduce blood flow to the wound for accelerated healing. The cooling band-aid may be kept refrigerated or frozen until ready to use. The coolant typically lasts for 10 minutes or more before requiring re-cooling in a refrigerator or freezer. The bandage may be used to control pain and swelling from a superficial injury or for dental pain by application to the cheek or inside the mouth in the form of a non-toxic cooling gel gauze.

A thermal regulating eye patch embodiment is provided for cooling or warming the eye or eye socket after, for example, surgery or injury to reduce swelling of the eye or surrounding tissue. Additionally, the patch may be used to treat styes. The patch includes soft thermal regulatory gel that may provide therapeutic cooling or warmth, depending on the selected thermal regulatory medium. For warming, the patch may be moistened and warmed with safe low voltage electric power or in a microwave oven. The patch may be battery powered to maintain thermal regulation with mobility. The eye patch may use adhesive to attach to the eye area or an elastic band or Velcro may used, as desired.

Generally, the present invention provides a therapeutic thermal regulation system for thermally regulating tissue and at least partially immobilizing a joint. The system includes one or more substantially flexible, at least partially thermally conductive housing, optionally activatable thermal regulatory medium in the housing, and one or more applicator adapted to apply the housing to the tissue. The applicator may be selected from the group consisting of (1) one or more splint, (2) one or more wrist splint, (3) one or more or elbow splint, (4) one or more knee or ankle splint (5) one or more cervical collar, (6) one or more TLSO apparatus, (7) one or more eye patch, (8) one or more adhesive bandage, (9) one or more cushion, (10) one more finger splint, (11) one or more glove or mitten, or (12) medium-filled hollow fiber fabric. The thermal regulatory medium may be selected from among the following media: activatable thermal chemicals, activatable thermal gels, activatable thermal microspheres, or circulating fluids including air or other gases, thermal chemicals, water, or gels.

Methods of using an optionally activatable thermal regulatory medium to regulate tissue temperature are also provided. One method, for example, involves housing the medium in an at least partially thermally conductive housing, coupling the housing to an applicator adapted to apply the housing to tissue, and activating the medium.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which:

FIG. 5 is a schematic illustration of the top view of the back panel of the head device of one embodiment of the present invention;

FIG. 5a is a frontal view of a back panel strip for cooling the spinal column of one embodiment of the present invention;

FIG. 6 is a schematic illustration of another embodiment of the present invention as placed on a medical patient portraying the side view.

DETAILED DESCRIPTION OF THE INVENTION

While the making and using of various embodiments of the present invention are discussed in detail below, it should be appreciated that the present invention provides many applicable inventive concepts that may be embodied in a wide variety of specific contexts. The specific embodiments discussed herein are merely illustrative of specific ways to make and use the invention and do not delimit the scope of the invention.

The present invention disclosed herein includes a head device and a cooling medium for cooling the head, neck and spine. Cooling of the head, neck and spine facilitates a reduction in swelling of the brain and surrounding tissue after injury, which helps to minimize long term damage to the brain. The present invention also encompasses a method for using the head device and for activating the cooling material to facilitate cooling of the brain after an injury.

It has been reported that approximately 20 percent of all head injuries are classified as severe and hence may potentially be life threatening. The overall effects of traumatic brain injuries are permanent and complex, thus, management of Central Nervous System (CNS) injury is of critical importance. Management of the effects of the injuries during the critical time period following severe brain injury or during what professionals in emergency medicine have termed the golden hour affects the survival and recovery of those individuals. This golden hour includes the time the patient is at the scene of the accident and the essential field stabilization and transport of the individual to a medical facility. The golden hour also includes a window of opportunity to determine how extensive the damage is to the brain. Neurologists may need to perform a CT scan to evaluate the extent of damage to the brain and to determine if there are bleeds, lesions contusions to the CNS, and/or fractures to the skull. On-scene intervention also includes procedures that are as unobtrusive as possible and limit damage to the brain. Current emergency protocols require checking airway, breathing, and circulation (ABC's)followed by neck and spinal stabilization when neck and back injury appears to be evident before transport.

The present invention is useful not only for emergency response personnel, but also for individuals who engage in sports or recreation where head protection or head cooling may be desirable. The present invention may be incorporated into helmets for bicycle and motorcycle riding, car racing, boxing, baseball, skate boarding, football, hockey, climbing, skydiving and other sport and recreational helmets. Other uses may be found in occupational helmets such as construction helmets, miner helmets and other head protection for work or dangerous environments. The cooling function of the present invention may be self activated by the user to cool the head for comfort or in the case of injury before emergency response personnel arrive.

Structure

Figure 1:
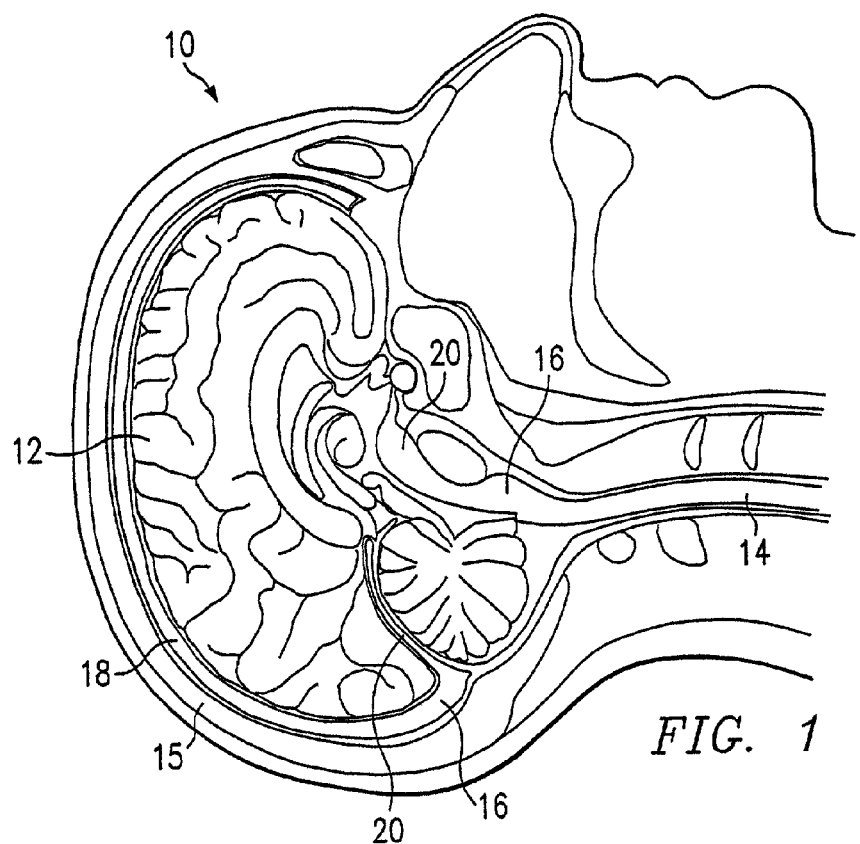
FIG. 1 is a cross sectional view of the brain with cerebrospinal fluid.

FIG. 1 is a cross sectional view of the brain with cerebrospinal fluid. The brain 12, as well as the spinal cord 14, is generally protected against injury by cerebrospinal fluid 16. The cerebrospinal fluid 16 circulates through the subarachnoid space 18 that is around the brain 12 and spinal cord 14. The cerebrospinal fluid 16 also circulates through the brain 12 via ventricles 20. Normally, cerebrospinal fluid 16 is absorbed as rapidly as it is formed. Cerebrospinal fluid generally leaves the body at the same rate it is produced, about 0.47 milliliters per minute, through the arachnoid space 18 at the top of the skull 15. The cerebrospinal fluid 16 is a clear, colorless, fluid having a watery consistency and contains vital nutrients including proteins, glucose, salts, and white blood cells. The cerebrospinal fluid 16 also circulates nutrients delivered via the blood.

Figure 1A:
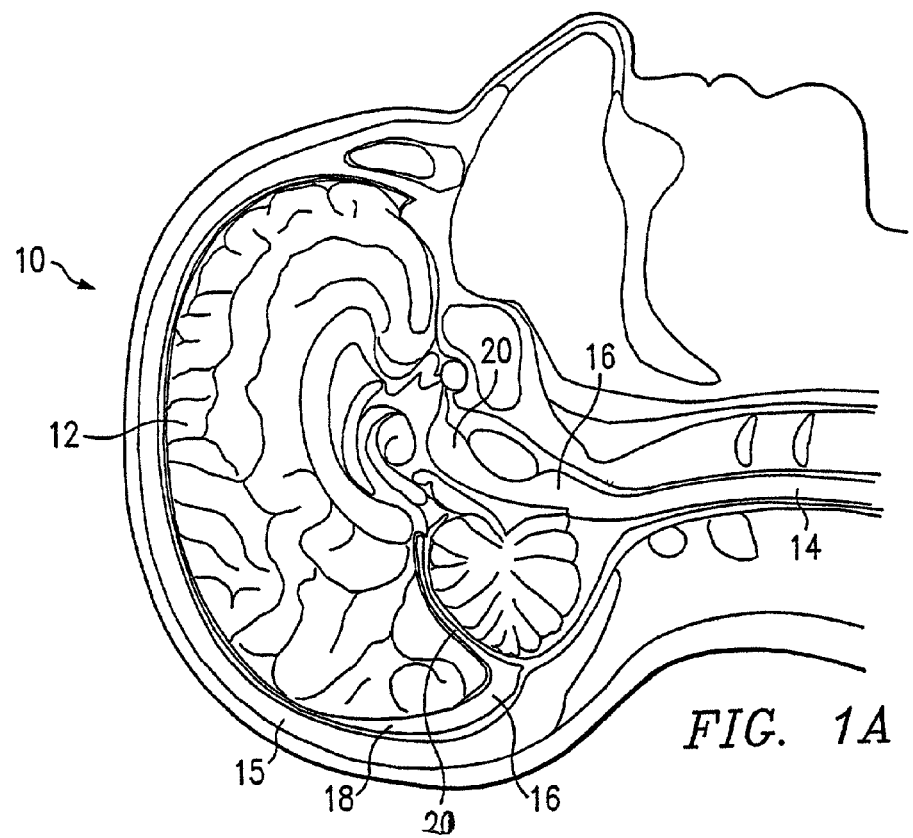
FIG. 1a is a cross sectional view of the brain with cerebrospinal fluid after a traumatic injury.

FIG. 1a is a cross sectional view of a brain having swelled against the skull 15. When a brain injury occurs there is primary physical damage that can kill or disable. But there are also secondary insults to the brain 12, which result from the swelling of the brain 12. When swelling occurs, the brain 12 will swell against the skull 15, thus blocking the flow of the cerebrospinal fluid 16 around the brain 12 and blocking the flow of nutrients through the ventricles 20. The internal pressure builds and squeezes blood vessels blocking the flow of blood which carries oxygen and nutrients to the brain. A reduction in the flow of nutrients to the brain 12 also causes secondary damage to the brain 12.

The build up of fluids 16 causes inter-cranial pressure (ICP) to build and the brain swells against the skull and blocks the exit point of cerebrospinal fluid 16. Pressing against the wall of the skull also damages the brain. All of the above cause additional or secondary injury to the brain. The elevation of the heart rate increases more blood to the injured area of the brain, thereby causing more damage due to swelling and the presence of blood destroying brain cells.

The present inventor has recognized that application of a cold element to the head, neck, and/or spine reduces the swelling of the brain and spinal cord after an injury and reduces the increased flow of blood by means of cooling the carotid artery. Reducing swelling is particularly important in emergency situations such as vehicle accidents which involve head and/or spinal cord injuries as there is eminent potential for build up of blood and cerebrospinal fluid in the cranial cavity. Damage is further intensified because the heart rate is increased as a natural response to trauma, thereby increasing profusion pressure (more blood to the injured site). In the case of penetrating or open head injuries, the problem of increased pressure due to blockage or exit capabilities is naturally reduced as the skull has been penetrated, but reducing the flow of blood to the area may help to reduce the amount of hemorrhaging.

Figure 2:
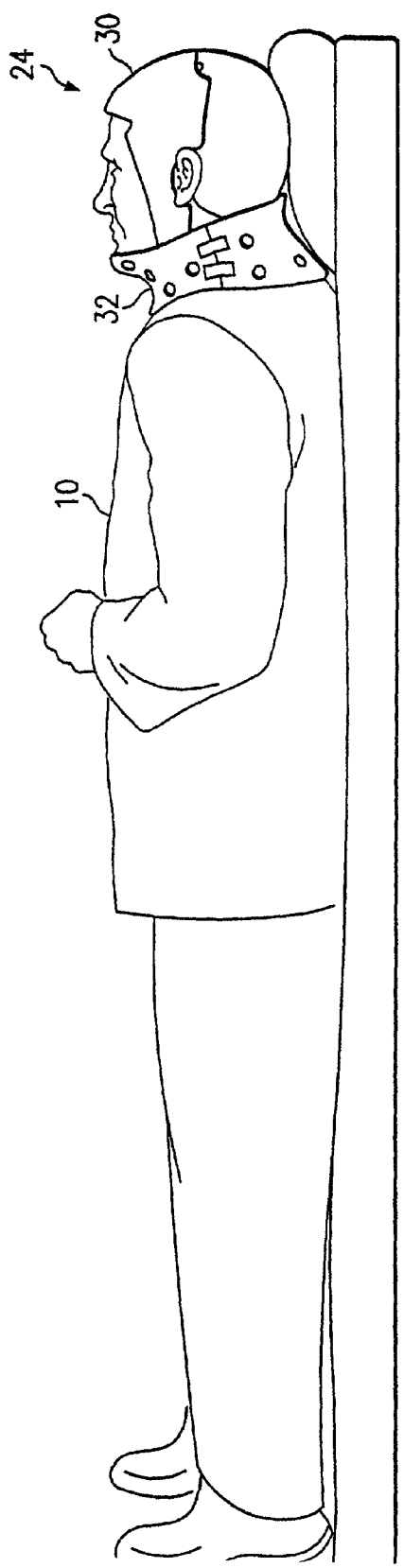
FIG. 2 is a schematic illustration of one embodiment of the present invention as placed on an accident individual portraying the left side view.

FIG. 2 is a schematic illustration of one embodiment of the present invention as placed on an accident individual. The accident individual 10 is found immobile at the scene of the accident. Emergency Medical Services (EMS) has standard guidelines by which treatment is administered to brain and spinal cord injury individuals. EMS will perform the ABC's and make an assessment using the Glasgow Coma Scale (GCS) which assesses the person's level of consciousness by eye opening, visual tracking, response to pain, and environmental stimulation to determine if a brain injury is suspected. If the person is unconscious, the stabilization of the head, neck, and back is completed. EMS personnel will be able to place the cooling system 24 on the head of the individual 10 in order to reduce intercranial pressure consequently reducing trauma to the brain and in turn, reducing or minimizing brain damage. The cooling system 24 is mounted on the head and neck of individual 10 through the use of head device 30 and neck brace 32. The cooling system 24 stabilizes and cools the head and neck of individual 10. The use of the cooling system 24 can be used in addition to current neurological protocols as an effort to reduce the need for a shunt, thereby reducing the need for invasive procedures to an already injured site.

Figure 3:
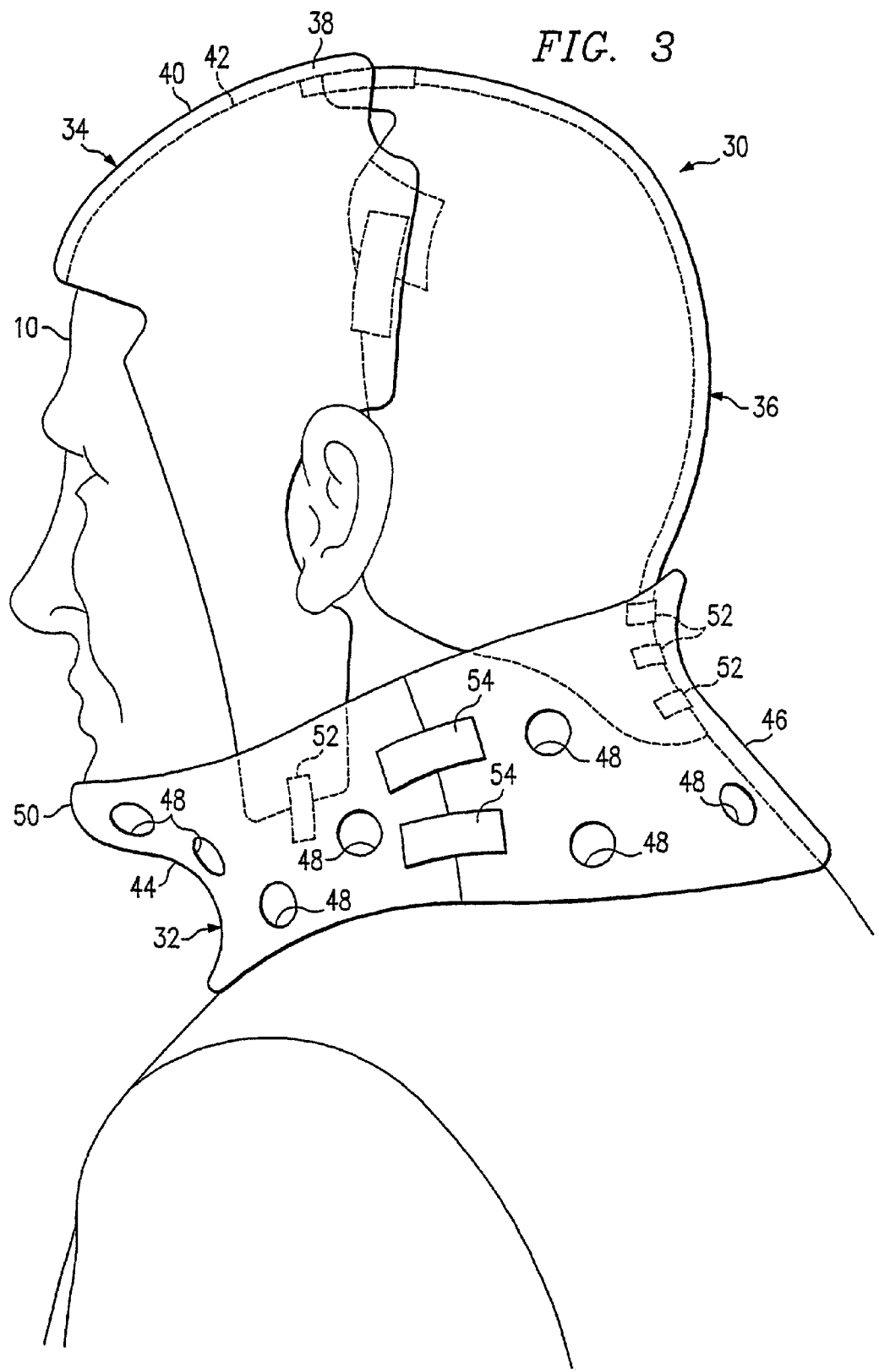
FIG. 3 is a schematic illustration of the left side view of one embodiment of the present invention in application.

Referring to FIG. 3, the head device 30 includes a top panel 34, a back panel 36, and a back panel strip 37 all of which are made of flexible material 38. Flexible material 38 may be, e.g., plastic, flexible foam, cloth, paper, or rubber. The flexible material 38 may have non-metallic properties that allow the head device 30 to be worn into a magnetic resonance imaging ("MRI") machine after individual 10 is brought to a medical facility. Head device 30 also includes a top layer 40 and bottom layer 42 that allow the cooling properties of cooling system 24 to be activated.

The neck brace 32 may include a front brace member 44, a back brace member 46, and one or more orifices 48 for air circulation. Neck brace 32 may also include a chin support 50 that permits the neck brace 32 to be more comfortably fitted to individual 10. The brace members 44 and 46 may include one or more inside fastening devices 52 and one or more outside fastening devices 54, that permit the brace members 44 and 46 to be fastened and permit the head device 30 to be interfaced to the neck brace 32 and provide a rigid support for the head of individual 10.

Figure 4:
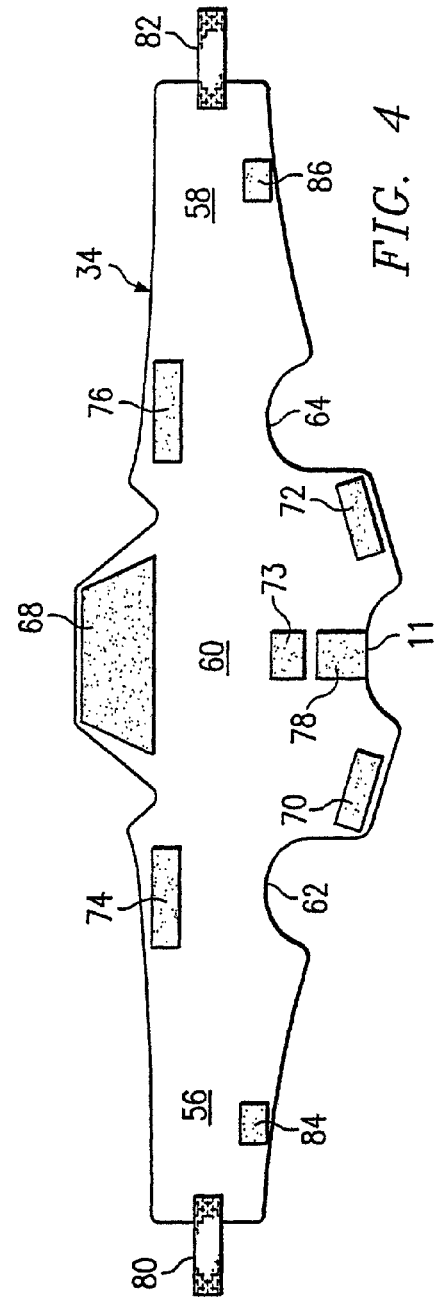
FIG. 4 is a schematic illustration of the top view of the top panel of the head device of one embodiment of the present invention.

Referring to FIG. 4, the top panel 34 having a substantially rectangular shape has a first elongated member 56, a second elongated member 58, and a central portion 60. The elongated members 56 and 58 extend from the central portion 60 of the top panel 34, which permit the central portion 60 to be positioned on top of the head of individual 10. The elongated members 56 and 58 are generally flush with the sides of the face of individual 10. Elongated member 56 and 58 extend down to facilitate cooling of the carotid arteries. The first and second elongated members 56 and 58 include a first recess 62 and a second recess 64, respectively, to provide openings for the ears of individual 10.

Accessibility to the ears of individual 10 allows EMS to provide medical treatment, if necessary, as bleeding from the ears can result from traumatic brain injuries. Accessibility to the ears of individual 10 also allows the patient to hear EMS personnel. The central portion 60 may include a third recess 71 for the hair of individual 10. The top panel 34 may further include a fastening device 68 (located on central portion 60), a left panel fastening device 70 and right panel fastening device 72 (also located on central portion 60). Left panel fastening device 70 is generally located below and adjacent fastening device 68 and is generally parallel to right panel fastening device 72, which is located below and to the right of the fastening device 68. The fastening devices 68, 70, and 72 are positioned to moveably connect to a fastening strap 73 that secures the head device 30 to individual 10.

The top panel 34 may also include a first and second reflective member 74 and 76, respectively, whereby the head of individual 10 is readily visible in dark and low visibility conditions. The top panel 34 may also include a bottom fastening device 78 located on central portion 60 that permits the back panel 36 to be connected and provides full coverage of the head of individual 10. The top panel 34 may also include left and right end tabs 80 and 82, located at the ends of elongated members 56 and 58, respectively. Located adjacent of end tabs 80 and 82 are end fastening devices 84 and 86.

Now referring to FIG. 5, the back panel 36 is depicted having an appendage 88, a first one or more fastening devices 90, a second one or more fastening devices 92, and a third one or more fastening devices 94. The one or more first fastening devices 90 are generally positioned in parallel on back panel 36 and used to connect the back panel 36 to the neck brace 32. The second one or more fastening devices 92 are fixedly attached to the back panel 36 and connect the sides of back panel 36 to the elongated members 54 and 56 of the front panel 34. The appendage 88 has an appendage fastening device 96 fixedly attached to the appendage 88. The appendage fastening device 96 of appendage 88 and the third one or more fastening devices 94 attach to the cooling strap 73 to secure the head device 30 to the head of individual 10. A back panel strip 37 (FIG. 5a) may be attached to the back panel 36 to facilitate cooling of the spinal cord area.

The cooling medium 98 may be any substance that provides cooling properties to the head device. The cooling medium may include chemical packets that are activated by application of pressure to the packet resulting in an endothermic reaction. The cooling medium may also include ice or generic ice packs that are refrigerated. The cooling medium generally will lower the temperature of the head approximately one to approximately two degrees and may include a large number of packets or changing of packets at predetermined intervals such that the head is cooled.

FIG. 6, depicts another embodiment of the present invention. The cooling system has a head piece 100 having an opening 102 and a cooling medium 98 which allows the face to be exposed for sight and breathing by the individual 10. The head piece 100 has a top layer 104 and bottom layer 106 and the cooling medium 98. The head piece 100 is suitable for non-emergency situations athletic events, such as boxing, where repeated blows to the head occur. The head piece 100 may also be worn when needed by traumatic brain injury patients that are in rehabilitation therapy when needed. Trauma to the brain requires extensive rehabilitation, which may lead to swelling from time to time and which causes setbacks in recovery. Patients in rehabilitation will generally feel a heating sensation. Such swelling and sensation may be reduced by application of the head piece 100.

Figure 7:
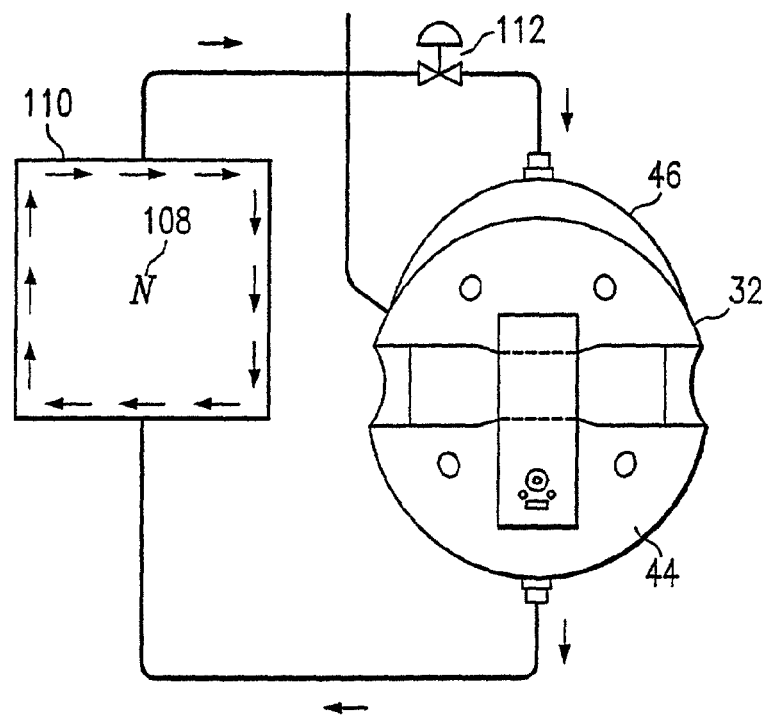
FIG. 7 is a frontal view of yet another embodiment of the present invention having a cooling element system fluidly connected to the head device.

FIG. 7 is cross-sectional view of yet another embodiment of the present invention. The neck brace 32 and cooling medium system 108 function as integral parts of the neck brace 32. Circulated through the front brace member 44 and the back brace member 46 are a chemical or chemical mixtures that act as coolants. The chemical or chemical mixtures are contained in a tank 110, and valves 112 that are interconnected to the front brace member 44 and the back brace member 46 regulate their circulation. The flow of chemicals allows for immediate reduction of swelling of the brain and may be, e.g. constant, intermittent or under the control of a temperature gauge or feed back system.

Figure 8A:
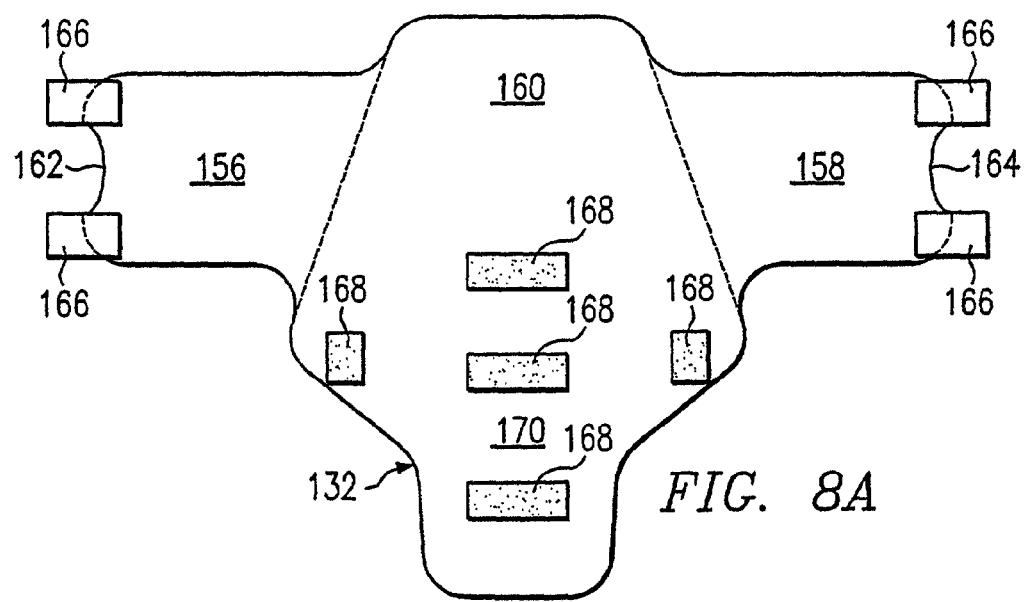
FIG. 8a is a back view of an alternative embodiment of the present invention.
Figure 8B:
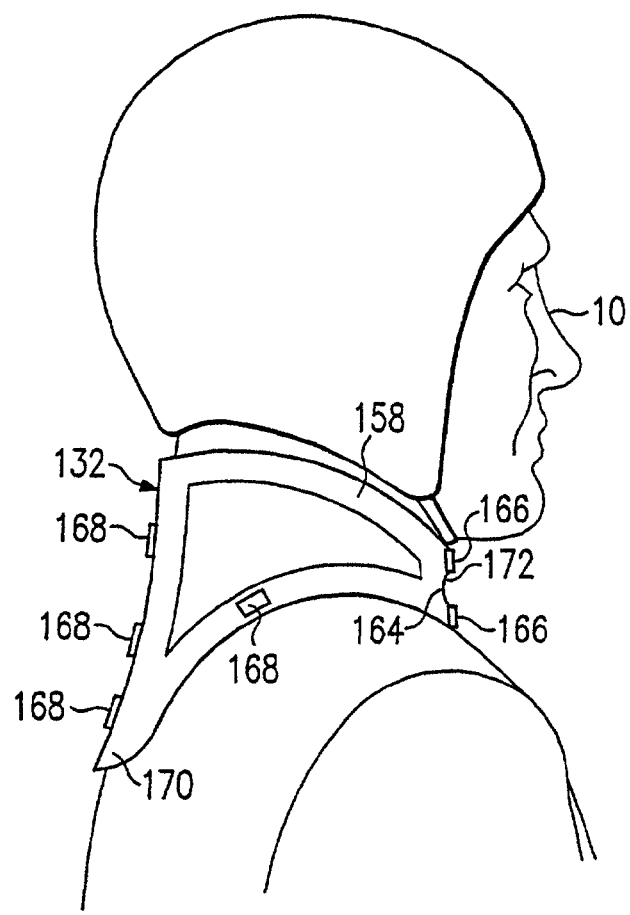
FIG. 8b is a side view of the embodiment of FIG. 8a shown being worn by an individual.

FIGS. 8a and 8b depict an alternative embodiment of the present invention. In the embodiment of FIGS. 8a and 8b, wrap-around flexible neck member 132 accomplishes cooling of the neck, and in particular cooling of blood flowing to the head from the carotid arteries of the neck. In FIG. 8a, neck member 132 houses activatable coolant as already described herein and comprises flexible flaps 156 and 158 extending from body 160 of neck member 132. Flaps 156 and 158 comprise cooperating perimeter contours 162 and 164 and cooperating fasteners 166. Additional fasteners 168 may be provided on body 160 of neck member 132 to provide means for attaching neck member 132 to optional components of the embodiment such as a back panel (previously described). Body 160 of neck member 132 further comprises spine support portion 170 extending from body 160.

FIG. 8b depicts the embodiment of FIG. 8a in operation as worn by an individual. Neck member 132 is placed on the back of the neck of individual 10 so that the back face of neck member 132, depicted in FIG. 8a, is distal to the neck of individual 10 and so that spine support portion 170 extends between the shoulder blades of individual 10. Flaps 156 and 158 are wrapped around the front of the neck of individual 10 and fastened together with fasteners 166 so that cooperating contours 162, 164 meet to form orifice 172 to provide access to the front of the neck of individual 10 for tracheotomy or other emergency procedures requiring access to the neck without compromising blood cooling. Neck member 132 houses coolant that may be optionally activated by individual 10 or by someone else in the event individual 10 is incapacitated. Optionally, neck member 10 may be provided with a port through which coolant may be circulated from an exterior source or to provide motive force to circulate coolant already housed in neck member 132. Further optionally, neck member 10 may be provided with an optionally inflatable lining that may be inflated to provide a secure fit around the individual.

The embodiment of FIGS. 8a and 8b provides a low cost, highly portable embodiment of the invention while preserving the function of cooling blood flowing to the brain from the carotid arteries of the neck to diminish swelling of the brain in the event of head trauma. The present embodiment further provides support for the neck and spine to minimize traumatic movement that might exacerbate the trauma.

Operation

In operation, if cooling medium 98 is resident in head device 30, such as a single-use or replaceable package, then cooling medium 98 is simply activated and the device 30 is placed on the patient. If the cooling medium 98 is stored outside the head device 30, the cooling medium 98 is activated and then placed within the head device 30. The cooling system 24 is then mounted on the head of individual 10.

The cooling system 24 is mounted by first placing the back panel 36 flat into the inside of back brace member 46 followed by aligning the first one or more fastening devices 90 of back panel 36 with the inside fastening devices 52 of back brace member 46. Fastening devices 90 and 52 are then connected. The top layer 40 of back panel 36 should face the inside of back brace member 46 such that the third one or more fastening devices 94 of back panel 36 are unencumbered by the back brace member 46. The combined back panel 36 and back brace member 46 are then carefully and strategically positioned to the back of the head of individual 10.

Next, the top panel 34 of head device 30 is placed on the top portion of the head of individual 10 with the top fastening device 68 of front panel 34 facing the face of individual 10. Once front panel 34 has been positioned so as to cover the top of individual's 10 head, elongated members 56 and 58 are brought down and around the individual's 10 face to the right and left respectively. As the two elongated members 56 and 58 are lowered, a first recess 62 and a second recess 64 are comfortably positioned around the ears of individual 10 within the recesses 62 and 64. The fastening device 68 of front panel 34 sits in close proximity to the eyes but generally do not cover them. The fastening device 78 of top panel 34 is attached to the fastening device 96 of back panel 36, providing full coverage of the head. The reflective members 74 and 76 should generally be readily visible at each side of the elongated members 56 and 58. The two elongated members 56 and 58 will generally meet at the bottom of individual's 10 chin. The left-end fastening device 80 and the right- end fastening device 82 allow, e.g., EMS, to pull gently to snugly fit to head of individual 10.

The front brace member 44 is placed around the front of individual's 10 neck and the elongated members 56 and 58 such that the chin of individual 10 sits comfortably in the chin support 50 of front brace member 44. The front and back brace members 44 and 46 will generally meet such that the one or more fastening devices are connected to secure the entire cooling system. The cooling strap 73 is then applied centeredly to the front fastening device 96 of top panel 34. Finally, the cooling strap is brought around to attach to the second one or more fastening devices 92 of top panel 34.

In addition to the foregoing embodiments, further embodiments of the invention are contemplated. One such embodiment provides top panel 34 with neck extensions 56, 58 and optionally other elements of the invention described herein above so that cooling is provided to the neck and particularly to blood flowing to the brain from the neck without requiring fitting a helmet over the user's head.

Neck cooling elements 56, 58 or 156, 158 and optionally other components of the invention may be incorporated into sports, recreational or occupational head protection whereby the cooling function may be optionally activated by the wearer for comfort, recovery from fatigue and/or heat, or in the case of emergency such as injury before emergency response personnel arrive. The cooling function may further be activated by a bystander in the event the wearer is incapacitated.

The present invention may further comprise one or more monitors to monitor important biological parameters of the individual such temperature, blood pressure, pulse rate and the like. Such a monitor may comprise one or more sensors in contact with the individual, or having remote sensing capabilities, to detect the desired biological parameter, and one or more displays to display the sensor readings. The monitor may be integral with the various embodiments of the invention described herein, such as sewn into the flexible material of the panels, or the monitor may be permanently or detachably attached or fastened to a panel or other element of the invention. Such detachable fastening may be accomplished with VELCRO fasteners, buckle and strap fasteners, ties, snaps or by any suitable means.

Figure 9:
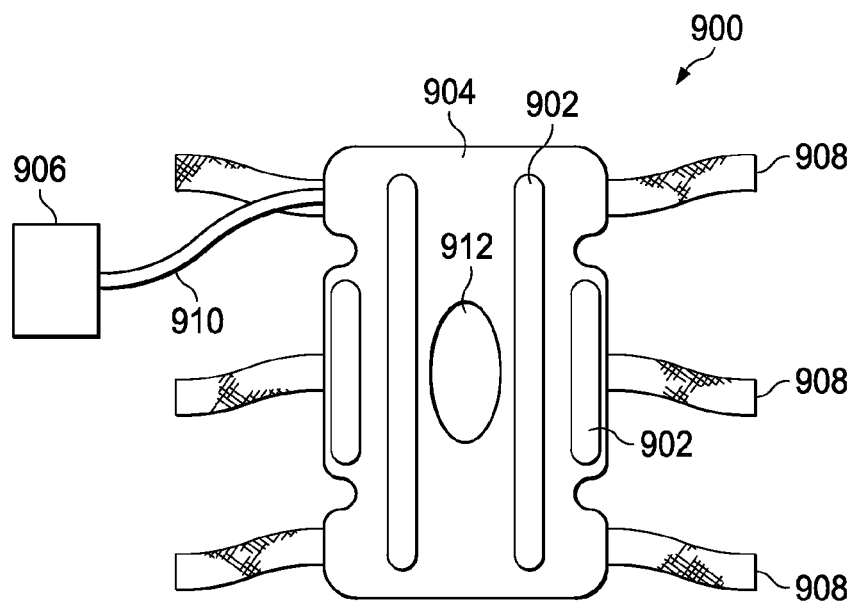
FIG. 9 is a cross sectional top view of a knee or elbow brace embodiment of the present invention.
Figure 10A:
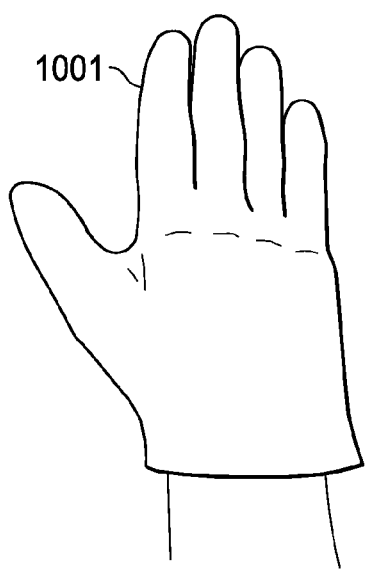
FIG. 10A is a top view of a glove embodiment of the present invention.
Figure 10B:
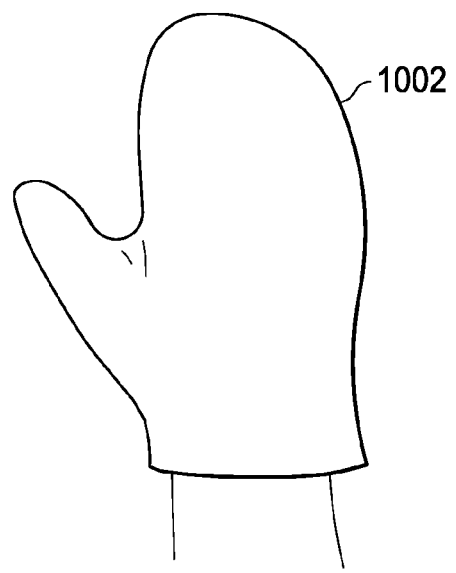
FIG. 10B is a top view of a mitten embodiment of the present invention.
Figure 10C:
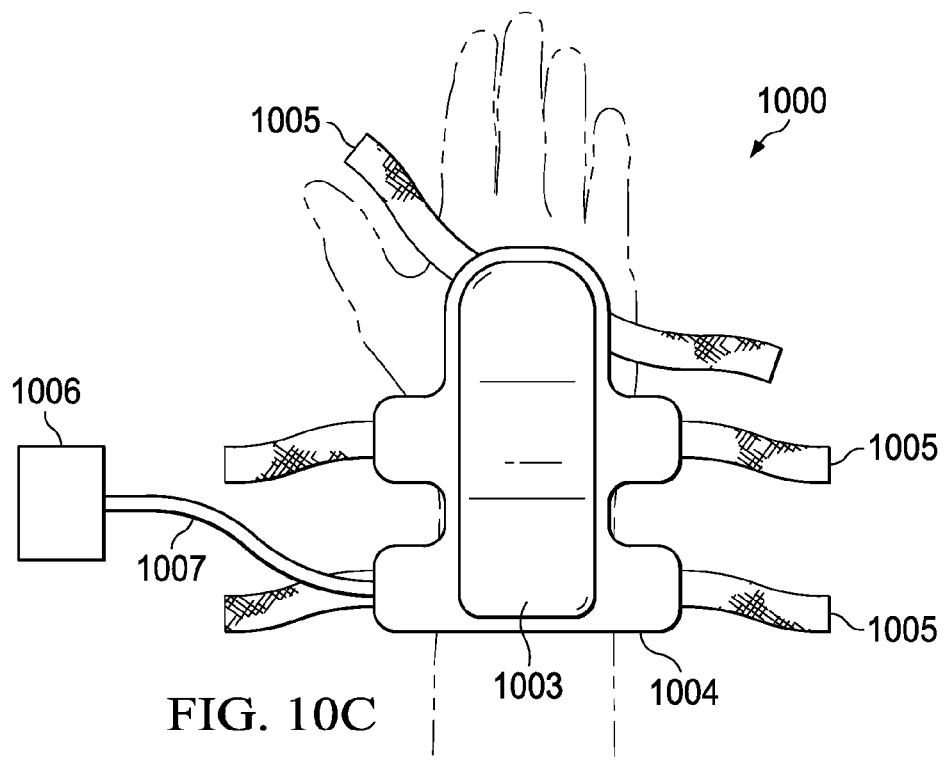
FIG. 10C is a cross sectional top view of a hand or wrist brace embodiment of the present invention.
Figure 10D:
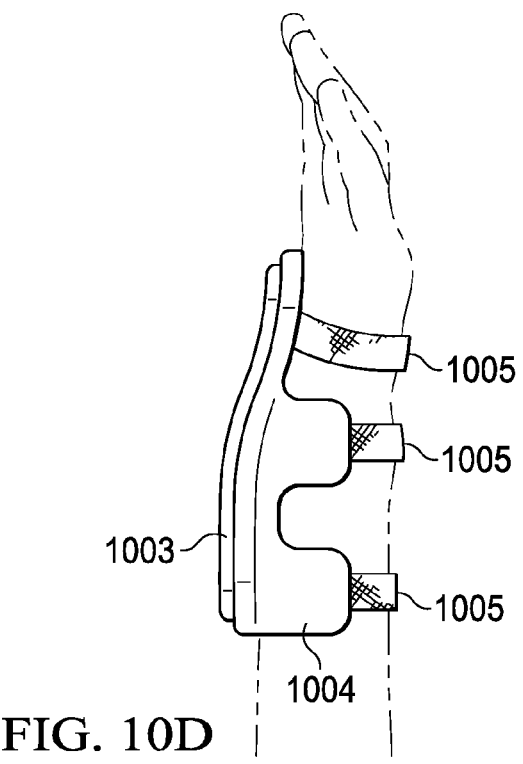
FIG. 10D is a cross section side view of the embodiment of FIG. 10C

A form-to-Fit knee or elbow cooling compression splint or brace system 900 of the present invention is illustrated in FIG. 9. A deformable yet substantially rigid splint 902 stabilizes or at least partially immobilizes a joint while gently compressing against swelling. To dissipate edema, cold panels or chemical cold packs 904 may be fastened to the interior or exterior of the splint with Velcro, snaps or other suitable fastener 908. Alternatively, splint 902 may be incorporated on the exterior or in the interior of cooling panels 904. In one embodiment, system 900 may have passive cold chemical activation packs or refrigeration gel packs. In another embodiment, splint 902 may be fluidly connected to an active coolant circulating system 906 by which cold fluid or cold air may be circulated by conduits 910 through a refrigerator in housing 906 and back to cooling packs 904. To fit different sized knees or upper or lower legs, splint 902 may be fabricated of flexible or deformable, yet substantially rigid material. System 900 may be adapted to a smaller size for the elbow joint or for lower extremity limbs such as the calf or shin.

A hand splint embodiment is shown in FIG. 10. Burn or trauma patients may wear glove 1001 or mitten 1002 which include interior partitions for housing a selected thermal regulatory medium such as coolant to reduce edema. FIGS. 10C and 10D depict hand/wrist splint or brace system 1000. Coolant may be supplied to splint system 1000 as described herein for other embodiments. Substantially rigid support 1003 at least partially immobilizes an injured hand or wrist while coolant packs 1004 provide soothing cooling and reduce edema. Alternatively, active cooling system 1006 may provide refrigerated coolant to cooling packs 1003 through conduit 1007. Some injuries to the hand or finger may make it difficult to slide a glove or mitten over the hand. System 1000, therefore, may be adapted to provide selectively fastenable and unfastenable portions 105 so that the system may be wrapped around an injured hand rather than slid over the hand. Hand splint system 1000 may be adapted provide sufficient freedom of movement so that the hand may be opened and closed for physical rehabilitation exercises during cooling treatment.

Figure 11:
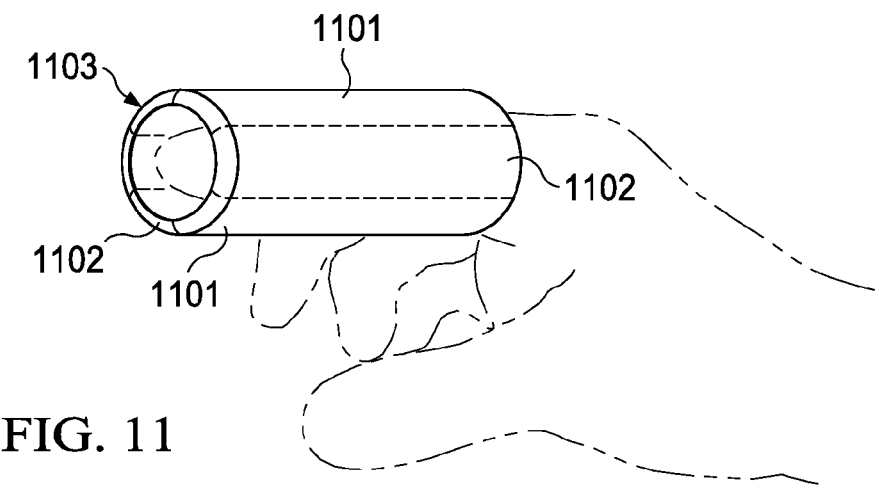
FIG. 11 is a perspective view of a finger splint embodiment of the present invention.

A finger splint embodiment is illustrated in FIG. 11. The finger embodiment includes substantially rigid portions 1101 and coolant reservoir partitions 1102, which cooperate to form a tubular sleeve 1103. Sleeve 1103 may be fitted over a finger in a manner similar to the toy called Chinese handcuffs or finger trap. Sleeve 1103 may be adapted to fit several fingers and may slide on to or wrap around a finger or fingers painlessly. As with the other embodiments described herein, the finger splint may be adapted for active or passive cooling. Sleeve 1103 may be useful for treating jammed, sprained, fractured or swollen hand or fingers and may require a substantially rigid structure for stiff splinting. The cooling system may be adapted to provide warming heat to treat arthritic joints, poor circulation or certain disabilities arising from stroke.

Figure 12:
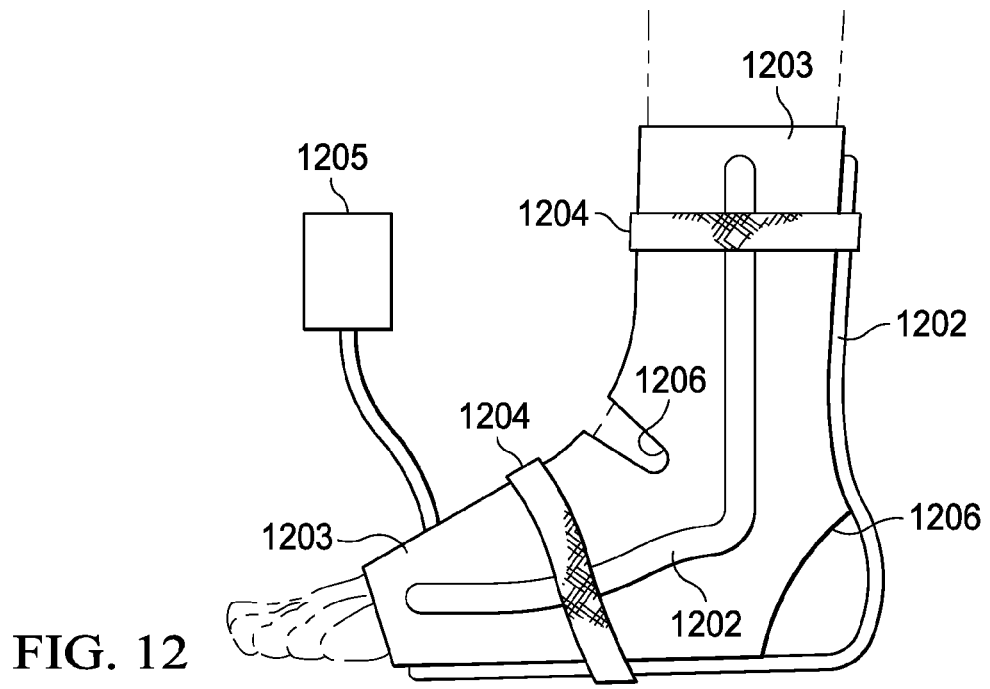
FIG. 12 is a cross section side view of an ankle brace embodiment of the present invention.

The present invention also provides an ankle compression cooling splint embodiment, shown in FIG. 12. Substantially rigid splint braces 1202 attached to the outside of panels 1203 by Velcro, straps, laces or snaps and the like to help at least partially immobilize the ankle joint. Panels 1203 may be cooled by passive gel, air, chemical coolant or active coolant circulation. Coolant panels 1203 may be configured in a figure "8" form to stabilize and cool the ankle. Alternatively to the figure "8" form, coolant panel 1203 may be adapted to wrap around the ankle and equipped with a substantially rigid brace. Also contemplated by the present invention is a tubular coolant sleeve that slides over or wraps around the ankle like a tube sock to provide cooling compression to the foot when worn inside a boot or shoe.

A cooling cervical collar immobilizer with a substantially rigid support is another embodiment of the cooling system of the present invention, as illustrated in FIG. 13. Any combination of splints 1301 in combination with cooling packs 1302 to substantially immobilize the neck and cool the carotid arteries are contemplated in the embodiment of FIG. 13. A substantially rigid support may be adapted with holes 1304 in the front, back and sides of the brace to allow access to the patient's neck for applying external cooling packs or for medical monitoring. Rigid structure 1301 may be located inside cooling pack 1302 and be formable to fit snugly around a patient's neck.

Figure 13A:
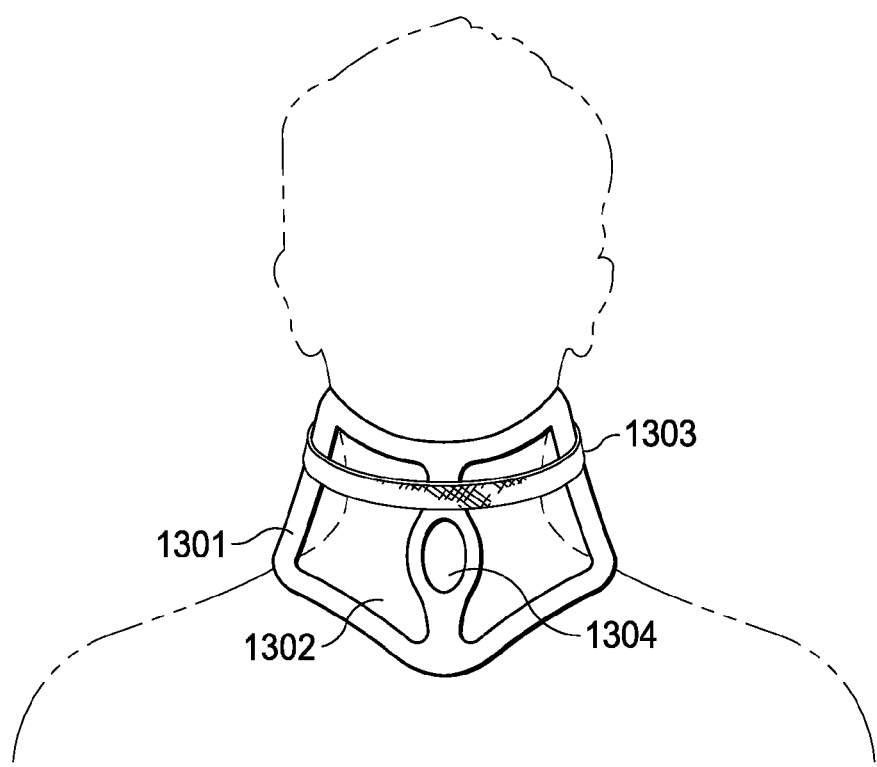
FIG. 13A is a cross section front view of a cervical collar brace embodiment of the present invention.
Figure 13B:
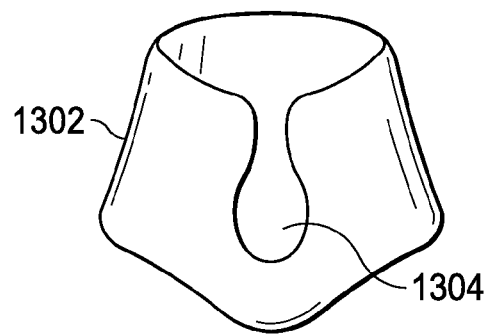
FIG. 13B is a top view of an alternate embodiment of FIG. 13A.
Figure 13C:
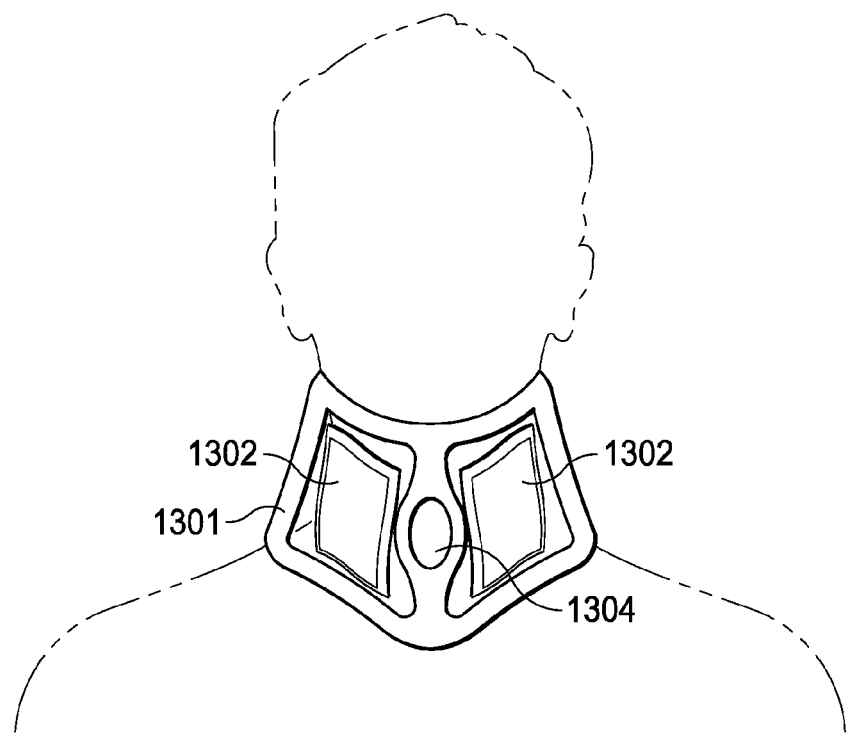
FIG. 13C is a cross section front view of another alternate embodiment of FIG. 13A.
Figure 13D:
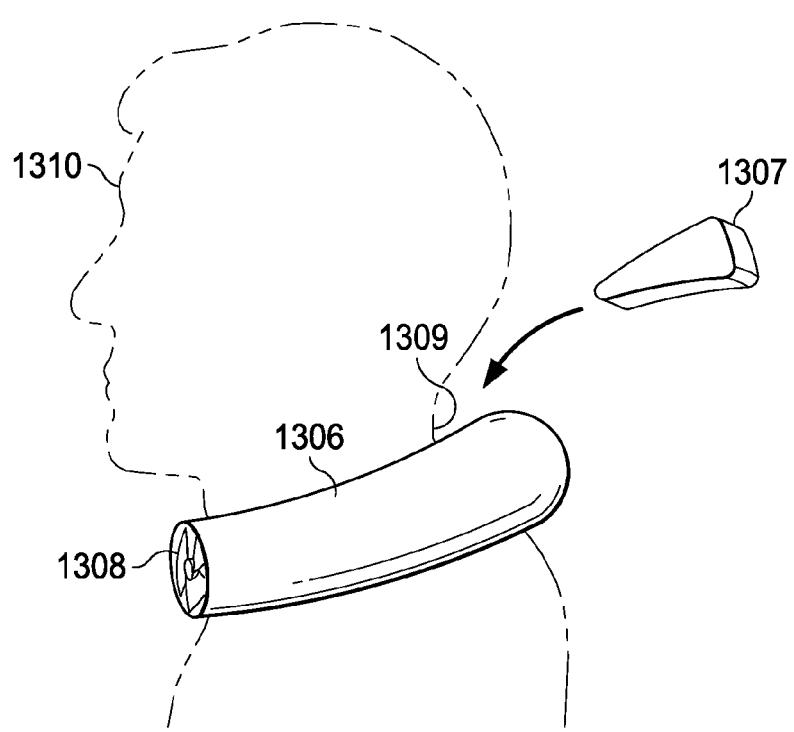
FIG. 13D is a side view of another cervical collar embodiment of the present invention.
Figure 13E:
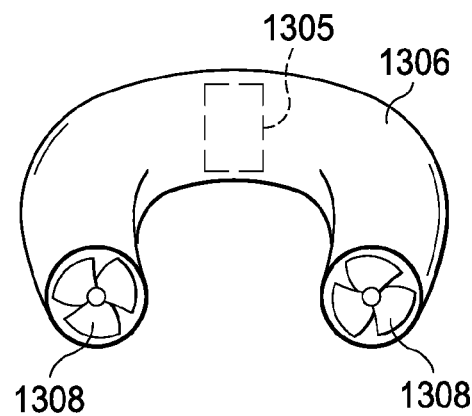
FIG. 13E is a top view of the embodiment of FIG. 13C.

Wedge-shaped coolant packs 1307 may be provided with a cooling cushion/cervical collar embodiment of the present invention as depicted in FIG. 13c. Cooling wedges 1307 may be placed between cooling cushion 1306 and neck 1309 to stabilize and at least partially immobilize head 1310. Cooling cushion 1306 includes a cooling system of the present invention such as fans 1308 powered by battery 1305. Cushion 1306 may include sponge or foam rubber in a shell of soft or substantially rigid plastic. Cushion 1306 may also, or alternatively, be at least partially inflatable with air, fluid or coolant to provide optionally adjustable sizes for a snug fit.

The cooling system of the present invention may be active or passive with cold gel, chemical, fluid or air. A self-contained cooling system kit of the present invention may be installed in an ambulance on an interior side panel, for example, or an active cooling system of the invention may be connected to the air conditioning system of the ambulance. Additionally, the system may be a mounted on a wall of a hospital such that active coolant may be plugged into the collar splint embodiment. The coolant may be air, water, gel, passive or active circulating fluid.

Figure 14:
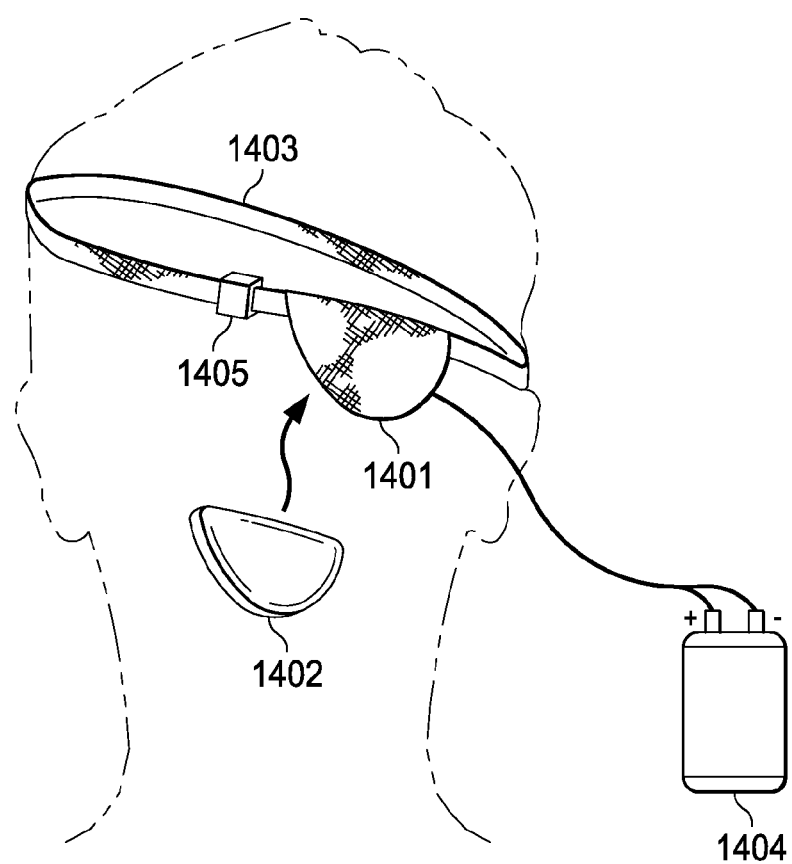
FIG. 14. is a perspective view of an eye patch embodiment of the present invention.

In FIG. 14, a thermal regulating eye patch embodiment is provided. Patch 1401 includes thin gel pack 1402 for optionally cooling or warming, depending on the selected gel medium, the eye or eye socket after surgery or injury, for example, to reduce swelling to the eye and surrounding tissue. Additionally, patch 1401 may be used to treat styes. Gel pack 1402 may be moistened and warmed with safe low voltage electric power or in a microwave oven to provide warmth in the alternative to cooling. Patch 1401 may use adhesive to attach to the eye area or an elastic band 1403 or Velcro may be used, as appropriate. Patch 1401 may be battery powered to cool or warm the gel pack 1402 for maintenance of thermal regulation with mobility.

Figure 15:
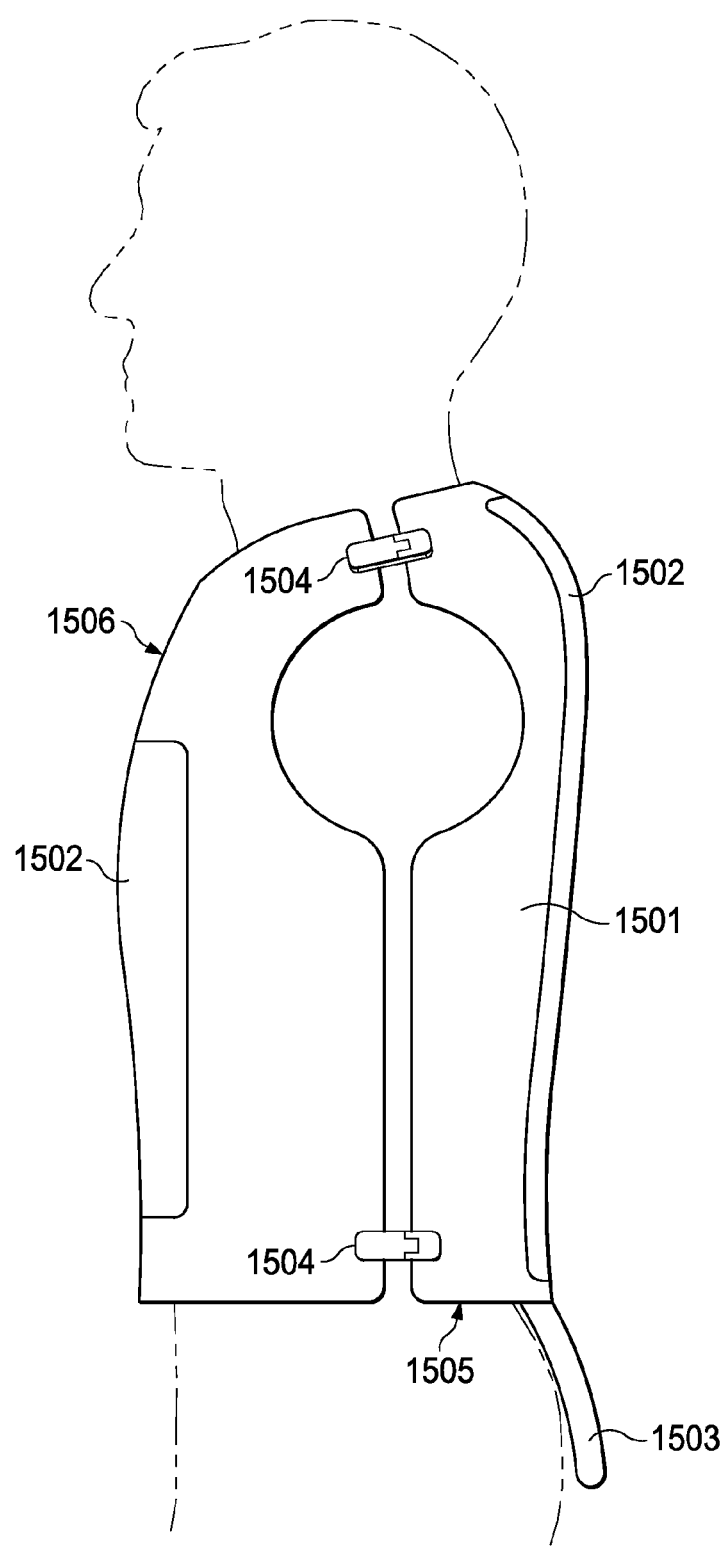
FIG. 15 is a cross section side view of a TLSO embodiment of the present invention.

A Thoracic, Lumbar, Sacral Orthopedic (TLSO) splint cooling system of the present invention is shown in FIG. 15. A cooling system for a splint to stabilize the upper torso is provided. The TLSO embodiment of FIG. 15 may include substantially rigid support 1501 and flexible cooling system panels 1502 attached to the interior or exterior of substantially rigid splint or brace 1501. Optionally attachable lower back support 1503 may also be included. Back moiety 1505 and front moiety 1506 may be secured around a patient by fasteners 1504. The TLSO embodiment may find utility for physical rehabilitation purposes.

Figure 16A:
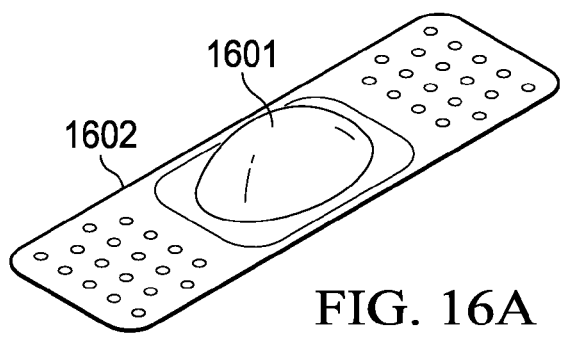
FIG. 16A is a perspective view of an adhesive bandage embodiment of the present invention.
Figure 16B:
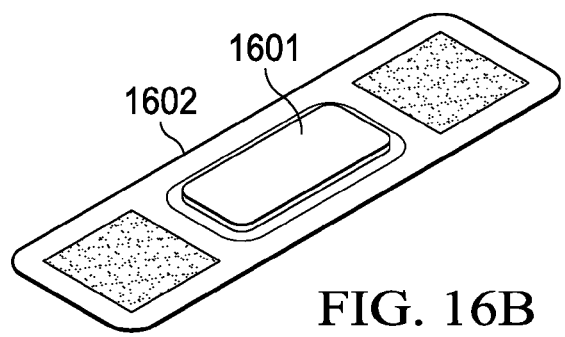
FIG. 16B is a perspective view of an alternate embodiment of FIG. 16A.
Figure 16C:
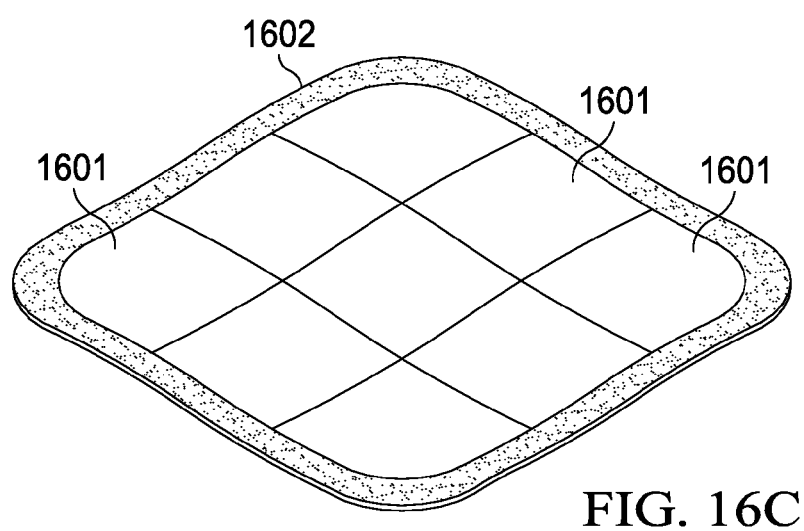
FIG. 16C is a top view of an another embodiment of the adhesive bandage of the present invention.
Figure 17A:
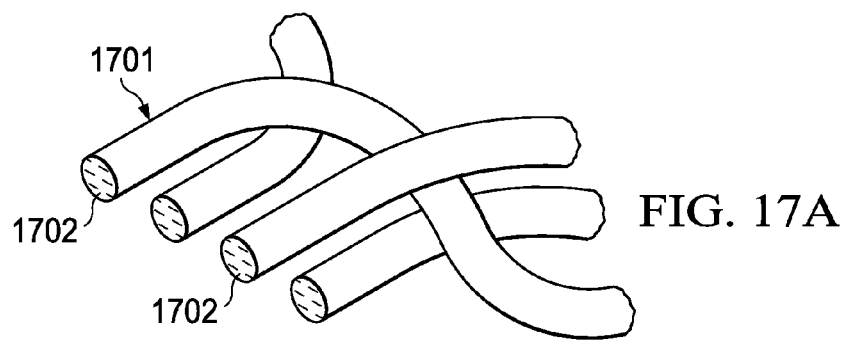
FIG. 17A is a magnified perspective view of hollow fibers of the present invention.
Figure 17B:
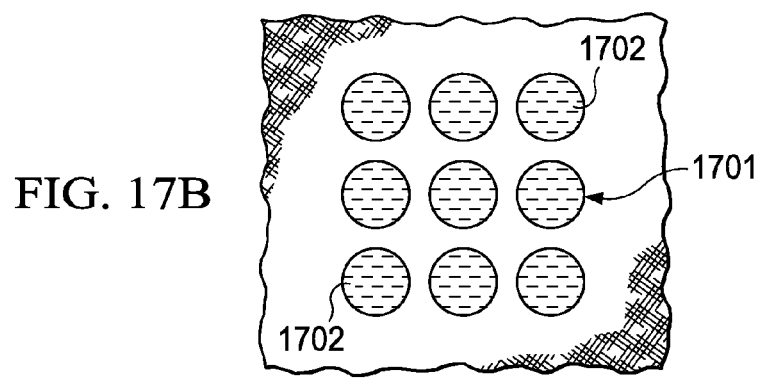
FIG. 17B is a cross section view of the fibers of FIG. 17A.
Figure 17C:
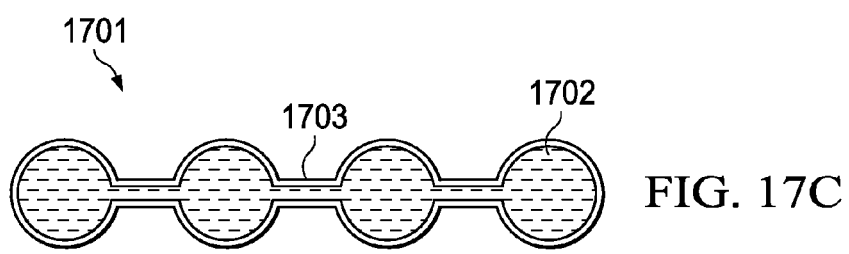
FIG. 17C is a magnified cross section view of an alternate embodiment of the hollow fibers of the present invention.
Figure 17D:
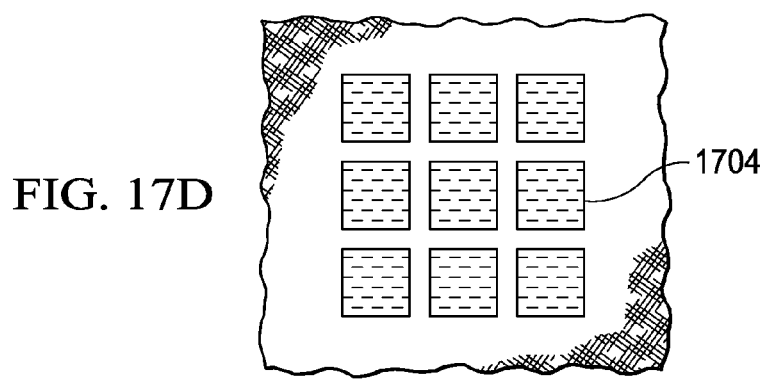
FIG. 17D is a magnified top view of another embodiment of the hollow fibers of the present invention.

A cooling adhesive bandage embodiment of the invention, provided for small cuts on the hand, finger or body, is illustrated in FIG. 16. While similar to common adhesive bandages, the present invention has the added advantage of providing a small thin gel pack 1601 on the interior or exterior of the adhesive strip 1602. The cooling adhesive bandage may be kept refrigerated or frozen until ready to use. The bandages may be provided in a variety of different sizes and shapes, including square, rectangular, circular, hourglass and so forth. Thin gel coolant slows and helps stop initial bleeding from a cut or sting. The coolant typically lasts for 10 minutes or more before requiring re-cooling in a refrigerator or freezer. The bandage may be used to control pain and swelling from a superficial injury or for dental pain by application to the cheek or inside the mouth in the form of a non-toxic gel gauze.

Micro-fiber cooling matrix fabric is depicted in FIG. 17. The fabric has hollow fibers 1801 such that voids 1702 of fibers 1701 may be filled with coolant, for example. The hollow fibers are typically no larger in internal diameter than a pin whole. Channels 1703 may be provided between fibers 1701 to facilitate coolant circulation. Alternatively, coolant may be provided in hollow cells 1704 that may be integrated into fabric or clothing.

The fabric may be useful in situations that require temperature regulation in an unregulated environment. Typically, the fabric is durable and may be elastic or flexible yet remain dry for comfortable wear. When worn, body movement circulates cooling fluid stored inside the fabric fibers. The fabric fibers may be vinyl, plastic polyester or other synthetic fabric, for example. The coolant fabric may be woven in a blend with natural fibers to provide comfort. The coolant may comprise passive fluid coolant combined with air much like the radiator of a car. Ordinary fabrics, such as cotton, wool, silk, synthetics or blends, may be woven or sewn with the cooling fiber to add a designer look and quality. A garment of the cooling fabric may be useful for warm environments to cool an individual or it may be combined with soft pads inside substantially rigid splints. The fabric may be used in clothing, shoes, hats or caps. The fabric may also be used in air conditioning systems in a vehicle, computer or home. Air blown across or through the matrix provides an environmental cooling system. The fabric may be utilized as a filtration system to cool any type of fluid.

The invention contemplates all modes of implementing the cooling function, including water, ice water, air, chemical coolants or refrigerants, electrical or mechanical cooling and so forth. Cooling may be accomplished by circulating coolant through the elements of the present cooling system, wherein the elements may comprise interconnectable channels for circulating the coolant medium through and among the elements of the system, or by activating stationary coolant housed in the elements of the present system.

A wheel chair cooling or warming cushion system embodiment is contemplated by the present invention. A passive or active circulation cooling system of the invention may be adapted into a wheel chair cushion, for example. A thermal regulation system may be attached to the chair to maintain free and independent roaming mobility for the user. The thermal regulation system may provide intermittent circulation modalities with temperature and pressure controls, including, for example, a thermostat, to prevent pressure sores. The cushion embodiment may find utility not only for wheelchairs but also for thermal regulation in extreme environmental conditions such as, for example, a stadium cushion.

Cooling may be activated by various means, including initiating an endothermic chemical reaction by, for example, bringing together previously isolated chemical components of a chemical coolant medium, and/or by opening a valve or port to introduce coolant into the system or to provide a motive force to circulate coolant already housed in the present cooling system.

The panels and braces of the invention may incorporate inflatable members that may be inflated to provide a snug and secure fit of the various elements around the wearer. The inflatable members may be inflated with a suitable fluid including air, water or even the coolant medium itself. The inflatable members may be inflated automatically by, for instance, pulling a tab or pin to release pressurized fluid into the inflatable member. Additionally or alternatively, the inflatable members may be inflated in a regulated manner by, for example, a fluid pressure regulator having a regulatable valve and optionally a pressure gauge, whereby the inflatable member may be regulatably inflated to a desired pressure.

Further embodiments include adapting the invention for use with animals, children and infants.

The foregoing description has been directed to particular embodiments of the invention in accordance with the Patent Statutes for the purposes of illustration and explanation. It will be apparent that many alternatives, modifications, and variations will be apparent to those skilled in the art in light of the foregoing disclosure. In particular changes may be made to the shape and size of the head piece and neck brace to accommodate all patients, including humans and animals.

What is claimed is:

1. A finger splint comprising:
    a substantially form fitting tubular body;
    one or more substantially rigid splint coupled with the body;
    one or more panels coupled with the body; and
    an activatable non-pressurized thermal regulatory medium housed in the one or more panels, wherein the thermal regulatory medium is integral with the panels and can be heated or cooled.

2. The finger splint of claim 1, comprising a substantially planar body wrapped around one or more fingers to form a tubular body.

3. The finger splint of claim 1, wherein the non-pressurized thermal regulatory medium is selected from the group consisting of activatable thermal chemical, activatable thermal gel, activatable thermal microspheres, or a thermal fluid.

4. An eye patch comprising:
    a substantially form fitting patch comprising a substantially rigid splint adapted to be secured in proximity to an eye;
    one or more panels coupled with the patch; and
    activatable non-pressurized thermal regulatory medium housed in the housing, wherein the thermal regulatory medium is integral with the panels and can be heated or cooled.

5. The eye patch of claim 4, wherein the non-pressurized thermal regulatory medium is selected from the group consisting of activatable thermal chemical, activatable thermal gel, activatable thermal microspheres, or a thermal fluid.

6. A system for thermally regulating a hand, the system comprising:
    one or more detachable panels adapted to the shape of a portion of the hand a substantially rigid splint adapted to the shape of the one or more detachable panels; and
    activatable non-pressurized thermal regulatory medium housed in the one or more panels, wherein the thermal regulatory medium is integral with the one or more panels and can be heated or cooled, wherein the panel is a strip in the shape of one or more fingers.

* * * * *